US007959930B2

(12) United States Patent
De Wit et al.

(10) Patent No.: US 7,959,930 B2
(45) Date of Patent: Jun. 14, 2011

(54) RESCUE OF INFLUENZA VIRUS

(75) Inventors: Emmie De Wit, Hamilton, MT (US);
Monique I. J. Spronken, Rotterdam
(NL); Ron A. M. Fouchier, Rotterdam
(NL); Albert D. M. E. Osterhaus,
Rotterdam (NL)

(73) Assignee: Abbott Biologicals B.V., Weesp (NL)

( * ) Notice: Subject to any disclaimer, the term of this patent is extended or adjusted under 35 U.S.C. 154(b) by 0 days.

(21) Appl. No.: 11/722,769

(22) PCT Filed: Dec. 22, 2005

(86) PCT No.: PCT/EP2005/057092
§ 371 (c)(1),
(2), (4) Date: Jun. 25, 2007

(87) PCT Pub. No.: WO2006/067211
PCT Pub. Date: Jun. 29, 2006

(65) Prior Publication Data
US 2008/0050401 A1     Feb. 28, 2008

Related U.S. Application Data

(60) Provisional application No. 60/641,003, filed on Jan. 4, 2005.

(30) Foreign Application Priority Data

Dec. 24, 2004   (EP) ................................... 04078527

(51) Int. Cl.
| A61K 39/145 | (2006.01) |
| A61K 39/00 | (2006.01) |
| A61K 39/12 | (2006.01) |
| A61K 45/00 | (2006.01) |
| A01N 63/00 | (2006.01) |
| C12P 21/06 | (2006.01) |
| C12N 7/01 | (2006.01) |
| C12N 15/00 | (2006.01) |
| C12N 5/00 | (2006.01) |
| C12N 15/86 | (2006.01) |
| A61K 39/285 | (2006.01) |

(52) U.S. Cl. ............... 424/209.1; 424/184.1; 424/204.1;
424/206.1; 424/278.1; 424/281.1; 424/93.6;
424/93.1; 435/69.1; 435/456; 435/235.1;
435/325; 435/320.1

(58) Field of Classification Search .................... None
See application file for complete search history.

(56) References Cited

U.S. PATENT DOCUMENTS

| 5,166,057 A | 11/1992 | Palese et al. |
| 5,578,473 A | 11/1996 | Palese et al. |
| 5,820,871 A | 10/1998 | Palese et al. |
| 5,854,037 A | 12/1998 | Palese et al. |
| 6,001,634 A | 12/1999 | Palese et al. |
| 6,544,785 B1 * | 4/2003 | Palese et al. ................. 435/325 |
| 6,649,372 B1 | 11/2003 | Palese et al. |
| 6,887,699 B1 | 5/2005 | Palese et al. |
| 6,951,754 B2 | 10/2005 | Hoffmann |
| 2003/0095987 A1 * | 5/2003 | Haller et al. ............... 424/206.1 |
| 2005/0054846 A1 * | 3/2005 | Webster et al. ............ 536/23.72 |
| 2006/0134138 A1 * | 6/2006 | Kawaoka et al. .......... 424/209.1 |

FOREIGN PATENT DOCUMENTS

| EP | 0 490 972 B1 | 8/1995 |
| EP | 1 317 559 | 11/2001 |
| EP | 1 194 580 B1 | 2/2007 |
| EP | 1 185 615 B1 | 8/2007 |
| WO | WO 00/60050 A2 | 10/2000 |
| WO | WO 01/04333 A1 | 1/2001 |
| WO | WO 01/83794 A2 | 11/2001 |

OTHER PUBLICATIONS

Herfst et al., Recovery of Human Metapneumovirus Genetic Lineages A and B from Cloned cDNA, 2004, Journal of Virology, vol. 78, No. 15, pp. 8264-8270.*
Neumann et al., Reverse Genetics Demonstrates that Proteolytic Processing of the Ebola Virus Glycoprotein Is Not Essential for Replication in Cell Culture, 2002, Journal of Virology, vol. 76, No. 1, pp. 406-410.*
Benton et al., Signal-Mediated Import of Bacteriophage T7 RNA Polymerase into the *Saccharomyces cerevisiae* Nucleus and Specific Transcription of Target Genes, 1990, Molecular and Cellular Biology, vol. 10, No. 1, pp. 353-360.*
Mena et al., Synthesis of biologically active influenza virus core proteins using a vaccinia virus-T7 RNA polymerase expression system, 1994, Journal of General Virology, vol. 75, pp. 2109-2114.*
Mena et al., Rescue of a Synthetic Chloramphenicol Acetyltransferase RNA into Influenza Virus-Like Particles Obtained from Recombinant Plasmids, 1996, Journal of Virology, vol. 70, No. 8, pp. 5016-5024.*
Neumann, et al., "Reverse Genetics of Influenza Virus," 287 Virology, pp. 243-250, (2001).
De Wit, et al. "Efficient generation and growth of influenza virus A/PR/8/34 from eight cDNA fragments," *Virus Research*, 103, (2004), pp. 155-161.
Hoffman, et al. "'Ambisense'" Approach for the Generation of Influenza A virus: vRNA and mRNA Synthesis from One Template, *Virology*, 267, No. 2, (2000), pp. 310-317.

(Continued)

*Primary Examiner* — Zachariah Lucas
*Assistant Examiner* — Benjamin P Blumel
(74) *Attorney, Agent, or Firm* — Finnegan, Henderson, Farabow, Garrett & Dunner, L.L.P.

(57) ABSTRACT

The invention relates to the field of influenza vaccine production. Influenza vaccines have been produced in embryonated hens' eggs for over 50 years, but recently there have been considerable efforts to develop cell culture systems for vaccine production. The invention provides a nucleic acid comprising an influenza gene segment and a bacteriophage polymerase promotor or a complementary strand of said nucleic acid, and a cell comprising such a nucleic acid capable of producing desired influenza virus. Furthermore, the invention provides a composition comprising a cell or material derived from a cell according to the invention and a virus or material derived from a viral particle according to the invention.

14 Claims, 6 Drawing Sheets

OTHER PUBLICATIONS

Figure 1:
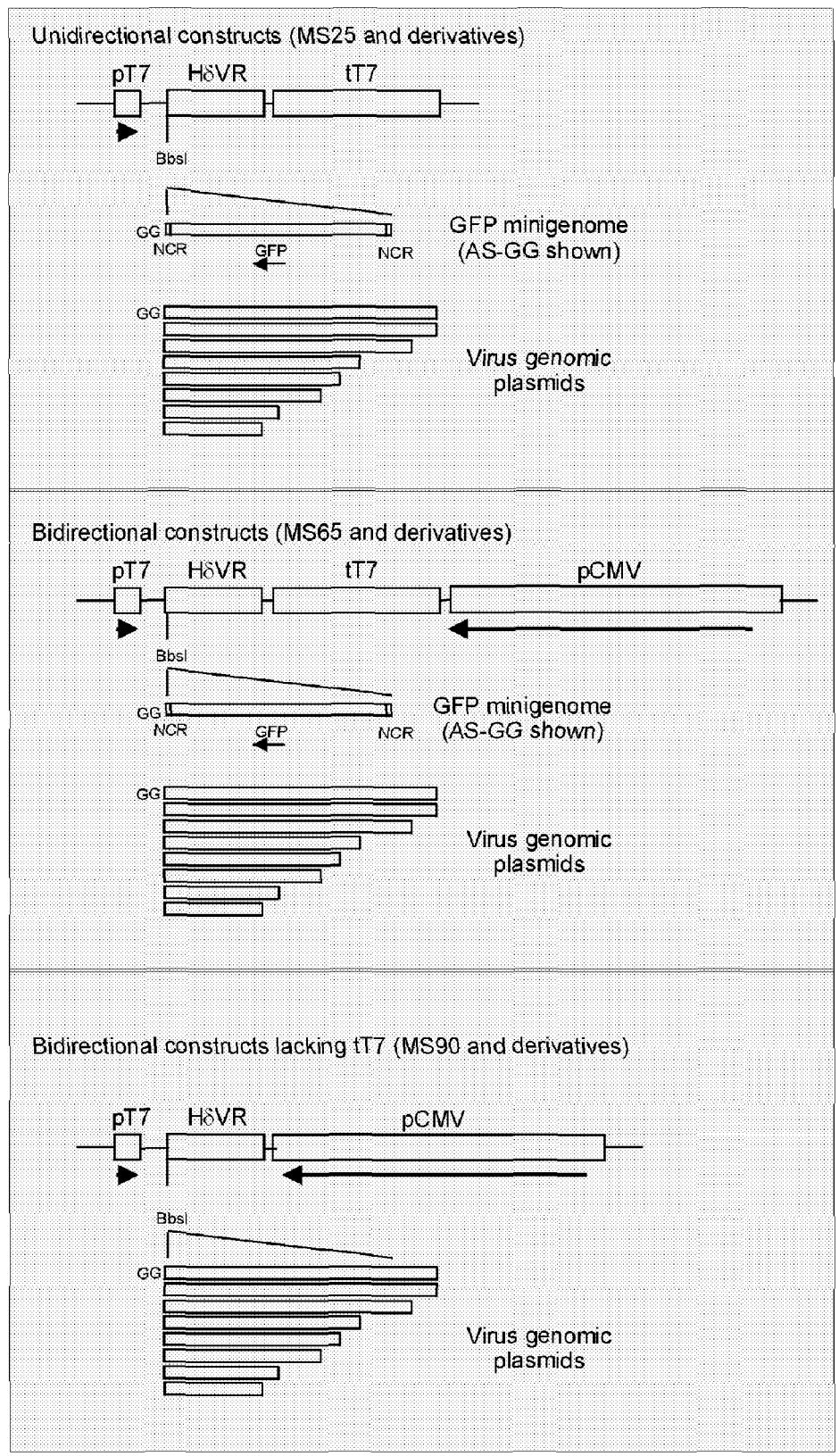

Neumann, et al. "Synthesis of influenza virus: new impetus from an old enzyme, RNA polymerase I," *Virus Research*, 82, (2002), pp. 153-158.

Neumann, et al.: "Reverse genetics of influenza virus." *Virology*, 287, (2001), pp. 243-250.

Lai, Michael M. C., "The making of infectious viral RNA: No size limit in sight," *PNAS*, vol. 97, No. 10, (2000), pp. 5025-5027.

Neumann, et al.: "Generation of influenza A viruses entirely from cloned cDNAs," *Microbiology*, vol. 96, (1999), pp. 9345-9350.

Pekosz, et al. "Reverse genetics of negative-strand RNA viruses: Closing the circle," *Proc. Natl. Acad. Sci.*, USA, vol. 96, (1999), pp. 8804-8806.

Fodor, et al. "Rescue of influenza A virus from recombinant DNA," *Journal of Virology*, vol. 73, No. 11, (1999), pp. 9679-9682.

Bridgen et al. "Rescue of a segmented negative-strand RNA virus entirely from cloned complementary DNAs," *Proc. Natl. Acad. Sci*, USA, vol. 93, (1996) pp. 15400-15404.

Schnell et al. "Infectious rabies viruses from cloned cDNA," *The EMBRO Journal*, vol. 13, No. 18 (1994), pp. 4195-4203.

Burkreyev et al. "Recombinant Respiratory Syncytial Virus from Which the Entire SH Gene Has Been Deleted Grows Efficiently in Cell Culture and Exhibits Site-Specific Attenuation in the Respiratory Tract of the Mouse," *Journal of Virology*, (1997) pp. 8973-8982.

Burkreyev et al. "Recovery of Infectious Respiratory Syncytial Virus Expressing an Additional, Foreign Gene," *Journal of Virology*, (1996), pp. 6634-6641.

Collins et al. "Production of infectious human respiratory syncytial virus from cloned cDNA confirms an essential role for the transcription elongation factor from the 5' proximal open reading frame of the M2 mRNA in gene expression and provides a capability for vaccine development," *Proc. Natl. Acad. Sci. USA*, vol. 92, (1995), pp. 11563-11567.

Luytjes et al. "Amplification, Expression, and Packaging a of a Foreign Gene by Influenza Virus," *Cell*, vol. 59, (1989) pp. 1107-1113.

De Wit, "Molecular determinants of influenza A virus replication and pathogenesis," University of Rotterdam (2006).

A. Zobel et al., 1993, "RNA polymerase I catalysed transcription of insert viral cDNA," *Nucleic Acids Res.* 21: 3607-14.

E. De Wit et al., 2007, "A reverse-genetics system for Influenza A virus using T7 RNA polymerase," *J. Gen. Virol.* 88: 1281-87.

* cited by examiner

RESCUE OF INFLUENZA VIRUS

The invention relates to the field of influenza virus vaccine production. Influenza viruses (Orthomyxoviridae) are enveloped negative-strand RNA viruses with a segmented genome (Taubenberger and Layne, Molecular Diagnosis Vol. 6 No. 4 2001). They are divided into two genera: one including influenza A and B and the other consisting of influenza C, based on significant antigenic differences between their nucleoprotein and matrix proteins. The three virus types also differ in pathogenicity and genomic organization. Type A is found in a wide range of warm-blooded animals, but types B and C are predominantly human pathogens. Influenza A viruses are further subdivided by antigenic characterization of the hemagglutinin (HA) and NA surface glycoproteins that project from the surface of the virion. There are currently 15 HA and nine NA subtypes. Influenza A viruses infect a wide variety of animals, including birds, swine, horses, humans, and other mammals. Aquatic birds serve as the natural reservoir for all known subtypes of influenza A and probably are the source of genetic material for human pandemic influenza strains.

Unlike the related paramyxoviruses, influenza viruses have a segmented RNA genome. Influenza A and B viruses have a similar structure, whereas influenza C is more divergent. Where the A and B type viruses each contain eight discrete gene segments coding for at least one protein each, the C type contains seven discrete segments, combining segment 4 and 6 of the A and B types. Influenza A and B viruses are covered with projections of three proteins: HA, NA, and matrix 2 (M2). Influenza C viruses has only one surface glycoprotein. Each influenza RNA segment is encapsulated by nucleoproteins (NP) to form ribonucleotidenucleoprotein (RNP) complexes. The three polymerase proteins are associated with one end of the RNP complex. RNPs are surrounded by a membrane with the matrix protein (matrix 1) as an integral part. The phospholipid portion of the envelope is derived from the cellular host membrane. Also found within the virus particle is nonstructural protein 2 (NS2).

World Health Organization (WHO) guidelines for nomenclature of influenza viruses are as follows. First, type of virus is designated (A, B, or C), then the host (if nonhuman), place of isolation, isolation number, and year of isolation (separated by slashes). For influenza A, HA and NA subtypes are noted in parentheses. For example, strains included in the recent trivalent vaccine for the 2000 to 2001 season are: A/Panama/2007/99 (H3N2), A/New Caledonia/20/99 (H1N1), and B/Yamanashi/16/98. Since 1977, there have been two influenza A subtypes cocirculating in humans: H1N1 and H3N2.

Influenza viruses accumulate point mutations during replication because their RNA polymerase complex has no proofreading activity. Mutations that change amino acids in the antigenic portions of surface glycoproteins may give selective advantages for a viral strain by allowing it to evade preexisting immunity. The HA molecule initiates infection by binding to receptors on certain host cells. Antibodies against the HA protein prevent receptor binding and are very effective at preventing reinfection with the same strain. HA can evade previously acquired immunity by either antigenic drift, in which mutations of the currently circulating HA gene disrupt antibody binding, or antigenic shift, in which the virus acquires HA of a new subtype. Antigenic drift pressures are unequal across the HA molecule, with positively selected changes occurring predominantly on the globular head of the HA protein. These changes also accumulate to a greater extent in HA than NA. Changes in other influenza proteins occur more slowly. Likewise, antigenic drift pressure is greatest in human-adapted influenza strains, intermediate in swine- and equine-adapted strains, and least in avian-adapted strains.

Because influenza viruses have a segmented genome, coinfection with two different strains in the same host can lead to the production of novel reassorted influenza strains containing different combinations of parental gene segments. Fifteen HA subtypes are known to exist in wild birds and provide a source of HAs that are novel to humans. The emergence in human circulation of an influenza strain with a novel subtype by antigenic shift has been the cause of the last two influenza pandemics in 1957 and 1968 and was most likely the cause of the 1918 influenza pandemic. To be concordant with all that is known about the emergence of pandemic influenza viruses, a pandemic strain must have an HA antigenically distinct from the one currently prevailing; this HA cannot have circulated in humans for 60 to 70 years; and the virus must be transmissible from human to human. In both 1957 and 1968, pandemics resulted from a shift in HA, and in both cases, HAs of pandemic strains were closely related to avian strains. Although one of the absolute requirements for a pandemic is that HA must change, the extent to which the rest of the virus can or must change is not known. Only the pandemic viruses of 1957 and 1968 are available for direct study, the 1918 pandemic influenza virus is being characterized using molecular archeology. In 1957, three genes were replaced by avian-like genes: HA, NA, and a subunit of the polymerase complex (PB1). In 1968, only HA and PB1 were replaced.

A specific diagnosis of influenza infection can be made by virus isolation, hemagglutination inhibition (HI) test, antigen detection by immunoassay, serological tests, demonstration of NA activity in secretions, or molecular-based assays. Specimens can be collected as sputum, nasopharyngeal swab, or nasopharyngeal washing obtained by gargling with a buffered-saline solution. The standard for influenza diagnosis has been immunologic characterization after culture. Serological analysis provides an accurate but retrospective method for influenza infection because it requires collection of both acute and convalescent sera.

Influenza viruses can be grown in embryonated hens' eggs or a number of tissue culture systems. The addition of trypsin (for the cleavage activation of HA) allows influenza virus propagation in Madin-Darby canine kidney (MDCK) cells and other lines. The primary method for vaccine production is still the cultivation of influenza viruses in eggs. Culture in cell lines is commonly used for the primary isolation of human influenza viruses (both types A and B). Many human influenza viruses can be cultivated directly in the allantoic cavity of embryonated eggs. Some influenza A and B viruses require initial cultivation in the amniotic cavity and subsequent adaptation to the allantoic cavity. After culture isolation, most influenza isolates are definitively identified using immunoassays or immunofluorescence. HA molecules of influenza viruses bind sialic acid residues on the surface of respiratory cells for the virus to gain entry.

Influenza strains can be characterized antigenically by taking advantage of the ability of influenza viruses to agglutinate erythrocytes in vitro. Anti-HA antibodies can inhibit agglutination. Thus, an haemagglutination inhibition (HI) assay is one of the standard methods used to characterize influenza strains. HI assays are used to determine whether sample strains are immunologically related (i.e., cross-reactive) to recent vaccine strains. Typing sera, generally produced in ferrets, are added to wells in a series of twofold dilutions, and laboratory workers score assay wells by looking for suspended versus clumped red blood cells. In most situations, a panel of sera is used for matching sample strains against vaccine and reference strains, and during any given influenza season, the vast majority of sample strains are successfully matched by HI assays. WHO provides guidelines and WHO Collaborating Centres provide guidance on the identification of antigenic characteristics of individual virus strains and can provide these strains to those wishing to obtain them. Sample strains are categorized according to immunologic pedigrees, such as A/Moscow/10/99 (H3N2)-like, A/New Caledonia/20/99 (H1N1)-like, and B/Beijing/184/93-like viruses. For sample strains that fail characterization in HI assays, laboratory workers must inoculate them into ferrets to produce a strain-specific antiserum. When the new antiserum is ready, HI assays are performed again as described. If the new serum shows significant gaps in cross-reactivity (usually defined as a fourfold difference between sample and vaccine strains), it is incorporated into the routine laboratory panel and used to look for new epidemic strains. Thus, HI assays are extremely important in the influenza virus surveillance effort for vaccine strain selection and are the most commonly used methods to assess antigenic drift.

Influenza strains can be characterized genetically by sequence comparison of the individual gene segments, and again WHO guidelines and WHO Collaborating Centers provide guidance on the identification of the individual identity of the RNA segments comprising the influenza genome; the influenza A and B virus nucleic acid segments encoding the nucleoprotein (NP), the basic polymerase 1 (PB1), the basic polymerase 2 (PB2), the acid polymerase (PA), the haemagglutinin (HA), the neuraminidase (NA), the matrixproteins (M1 and M2) and the nonstructural protein (NS1 and NS2), and the influenza C virus nucleic acid segments encoding the nucleoprotein (NP), the basic polymerase 1 (PB1), the basic polymerase 2 (PB2), the haemagglutinin-neuraminidase like glycoprotein (HN), the matrixproteins (M1 and M2) and the nonstructural protein (NS1 and NS2).

Requests for reference strains, e.g for antigenic analysis, for nucleic acid sequence comparison and for identifying vaccine viruses can be addressed to the WHO Collaborating Centre for Reference and Research on Influenza, 45 Poplar Road, Parkville, Victoria 3052, Australia (fax: +61 3 9389 1881, web site: http//www.influenza centre.org); the WHO Collaborating Centre for Reference and Research on Influenza, National Institute of Infectious Diseases, Gakuen 4-7-1, Musashi-Murayama, Tokyo 208-0011, Japan (fax: +81 42 5610812 or +81 42 5652498); the WHO Collaborating Center for Surveillance, Epidemiology and Control of Influenza, Centers for Disease Control and Prevention, 1600 Clifton Road, Mail stop G16, Atlanta, Ga. 30333, United States of America (fax: +1 404 639 23 34); or the WHO Collaborating Centre for Reference and Research on Influenza, National Institute for Medical Research, The Ridgeway, Mill Hill, London NW7 1AA, England (fax: +44 208 906 4477). Updated epidemiological information is available on WHO's web site at http://www.who.int/influenza and the geographical information system, FluNet, at http://www.who.int/flunet Awareness of the impact of influenza and of the health and economic benefits of its prevention is increasing, and the past decade has seen the use and benefits of vaccination and a number of anti-influenza drugs rise considerably. As a result of longer life expectancy in many countries, many more people are at risk of complications, the burden on the health care systems during influenza epidemics is more widely acknowledged, and more frequent international travel has created opportunities for the spread of the virus, while the introduction of new products has increased options for prevention and treatment of the disease. About 50 countries have government-funded national influenza immunization programs and the vaccine is available in many others. Specific recommendations for the use of the vaccine vary, but generally involve annual immunization for individuals of advanced age and those aged over 6 months who are at increased risk of severe illness because of a pre-existing chronic medical condition. In some countries, vaccine is used to reduce the spread of influenza to those at increased medical risk. Member States need to consider the benefit of influenza prevention activities in the context of their overall public health priorities.

Inactivated vaccines are classified into several types, depending on whether they contain whole virus particles, partially disrupted virus particles (split vaccines) or purified envelope antigens (subunit vaccines). Some subunit vaccines have been combined with an adjuvant or delivery system.

A few countries have licensed live attenuated influenza vaccines for certain target groups. Two different formulations of 1 vaccine have been used in healthy adults and children in the Russian Federation, and another live vaccine has been tested extensively but is not yet licensed. Until live attenuated vaccines are more widely available, they are not yet generally recommended for influenza prevention.

Two classes of antiviral agents have been developed for prevention and treatment of influenza. The M2 inhibitors, amantadine and rimantadine, are limited to treatment of influenza A viruses and have also been reported to be effective in prevention of infection. While both products cause some side-effects, significant neurological side-effects are more common with amantadine. Neuraminidase inhibitors, such as zanamivir and oseltamivir, have recently been licensed for treatment of types A and B influenza in a number of countries, and have been reported to be effective for prophylaxis. Resistant mutants have been detected in patients receiving both classes of antiviral agent. While this is not currently considered an important public health problem, the situation may change if these drugs are used on a very large scale.

WHO maintains a global international surveillance program operated with the cooperation of 110 national influenza centers located in 82 countries and 4 WHO collaborating centers for influenza reference and research located in Atlanta (United States), London (United Kingdom), Melbourne (Australia) and Tokyo (Japan). These centers provide an early warning system for emerging strains with epidemic potential. This system is important because the efficacy of the influenza vaccines is reduced if they do not contain the strains currently circulating. WHO issues recommendations for vaccine composition, as can be found in the Weekly Epidemiological Record (for example see issue 9, 2004, 79, page 88 or http://www.who.int/wer) published by the World Health Organization, in February for vaccines used in the northern hemisphere and in September for vaccines used in the southern hemisphere. As influenza has less defined seasonal patterns in equatorial regions, epidemiological considerations will influence which of these recommendations (February or September) is appropriate for vaccines for use in equatorial countries.

The collaborating centers carry out antigenic and genetic analysis of influenza isolates submitted by the national centers. Where evidence of antigenic variation is observed, this is collated with epidemiological data to assess the epidemiological significance of variants. Representative isolates are compared with the current vaccine strains using panels of human sera collected prior to and after vaccination, to assess whether current vaccines could be expected to protect against these viruses. Following publication of WHO's annual vaccine recommendations, high growth strains are developed and provided to manufacturers as reference viruses to assist in the generation of seed viruses for vaccine production. Tests for safety and potency of influenza vaccines include virus inactivation, microbial sterility, measurement of chemicals used for disrupting the virus and confirmation of the recommended antigen concentration. It is recommended that vaccines should comply with WHO requirements, however, the national control authorities should approve the specific vaccine viruses used in each country. National public health authorities are responsible for recommendations regarding the use of the vaccine. Also WHO has published recommendations on the prevention of influenza virus infections. (See WER No. 35, 2002, pp. 281-288.) Influenza vaccines have been produced in embryonated hens' eggs for over 50 years, but recently there have been considerable efforts to develop cell culture systems for vaccine production. The conventional standard methodology in embryonated hens' eggs is extremely cumbersome and has some major disadvantages: millions of eggs are required; in US more than 100 millions per season, eggs must be inoculated and harvested individually; extensive purification is required with a number of filtration and centrifugation steps to ensure freedom from egg protein to minimize risk of allergies; many production steps are required which are difficult to automate and are labor intensive, not to say time consuming and subject to contamination.

There has thus been a long standing need in the industry to develop vaccine production technology which demonstrates advantages over current vaccine production technology, i.e. by developing manufacturing protocols that will utilize special strains of cells capable of supporting growth of influenza virus and are adapted to growth in automated bioreactors, on biocarriers or in other cell-culture systems, to replace existing vaccine manufacturing methodology.

Often, well characterized continuous cell lines, such as VERO cells or other cells of primate origin, are suggested for use in influenza virus vaccine production. However, registration authorities nowadays shy away from vaccines produced in primate cells that are intended for human use. More and more, such authorities recommend that all products derived from primate (such as Vero) cells be free of residual intact cells and express continued concern about the level of residual material, such as primate cell DNA in products manufactured in these cells. Although the World Health Organization (WHO) currently accepts a limit of residual DNA from continuous cell lines of 10 ng per dose for viral vaccines when administered parenterally, registration authorities continue to consider the level of risk posed by residual primate cell material such as DNA on a case-by-case basis for viral vaccines.

For a long time the fundamental research of influenza A viruses has been hampered by the lack of availability of efficient reverse genetics systems. Although the earliest reverse genetics techniques for negative stranded RNA viruses were in fact developed for influenza A virus, the rescue of this virus exclusively from recombinant DNA was achieved only recently.

Recombinant influenza virus was produced upon transfection of eukaryotic cells with a set of eight plasmids from which each of the genomic viral RNA (vRNA) segments was transcribed by RNA polymerase I and a set of four additional plasmids expressing the nucleoprotein (NP) and the polymerase proteins PB1, PB2, and PA. The reported efficiencies of virus production using these 12-plasmid systems were relatively low.

Upon co-expression of five additional plasmids encoding the hemagglutinin (HA), neuraminidase (NA), matrix proteins 1 and 2 (M1 and M2) and non-structural protein 2 (NS2), virus titers in the supernatants could be increased. An elegant modification of these 12 and 17-plasmid systems is the implementation of bidirectional vectors to reduce the number of transfected plasmids to eight. With this system, the negative-stranded vRNA and the positive-stranded mRNA can be synthesized from the same plasmid.

The ability to produce recombinant influenza A virus facilitates future influenza virus research, however, no practical solution has yet been found to use recombinant influenza A virus obtained by reverse genetics techniques to sufficiently high titers in vaccine production, given the fact that most, if not all cell systems used in vaccine production do not or only little allow for replication of the above described recombinant viruses due to incompatibility between the polymerases involved in the reverse genetics systems and the cell species most often used.

Influenza A virus is a negative strand RNA virus. This means that in one replication cycle, three types of RNA are produced: negative sense vRNA, positive sense cRNA and positive sense mRNA. Unlike the viral RNA (vRNA) the mRNA is capped and has a poly(A) tail. The first A residues of the poly(A) tails of mRNAs match a short stretch of U residues in the genome that is regarded as the transcription stop/polyadenylation signal. It is thought that the polymerase when it reaches this stretch of U residues undergoes repeated cycles of backward slippage and in this way creates the entire poly(A) tail of the mRNA.

SUMMARY OF THE INVENTION

The invention provides a reverse genetics system for influenza virus that can be applied in cell types of different species. Polymerase I is a nucleolar enzyme that transcribes ribosomal RNA and is abundantly expressed in growing cells. rRNA, like vRNA has no cap and no poly(A) tail and polymerase I can therefore be used for the production of vRNA from cDNA. Transcription of viral cDNA by polymerase I allows the generation of virus like RNAs with correct 5' and 3' ends. However, whereas the transcription machinery of polymerase II is often compatible with genes from different species, polymerase I transcription exhibits stringent, though not absolute, species specificity. This species-specificity is conferred by the interaction of the transcription factors with the promoter and, to a lesser extent, in the protein-protein interactions between the factors. The species-specificity of the polymerase I-based reverse genetics systems is a major disadvantage for vaccine development, for one because the polymerase I promoters for cell species other than human, such as a canine or avian polymerase I promoter have not yet been described where in the industry, well defined canine (i.e. Madin Darby Canine Kidney (MDCK)) or avian cells (chicken embryo fibroblast (CEF)) are often used for influenza virus vaccine production.

The invention provides a nucleic acid comprising an influenza gene segment and a bacteriophage polymerase promotor or a complementary strand of said nucleic acid. Contrary to the finding of Neumann & Kawaoka (Virology 287, 243-240, 2001) indicating that in contrast to non-segmented viruses, a conspicious exception where T7 polymerase was thought not to work was influenza virus, whose generation involves the added complexity of synthesis of eight viral RNAs, in addition to the polymerase and nucleoprotein from cloned cDNA, the invention provides significant flexibility with respect to the plasmid vectors for this bacteriophage-polymerase-based reverse genetics technology, and the elements that they contain. For example, we used the RNA polymerase of bacteriophage T7 to produce vRNA or cRNA-like RNA molecules but various other RNA polymerases such as the bacteriophage SP6 RNA polymerase may be used. In a preferred embodiment, the invention provides a nucleic acid comprising an influenza gene segment and a T7 promotor or a complementary strand of said nucleic acid allowing us to base the system of the invention on expression of the gene segments of influenza virus under control of a T7 promoter. In one embodiment, a polymerase terminator is lacking. It is preferred that said nucleic acid has been provided with one or two additional guanine residue next to the promotor. For vaccine purposes, a nucleic acid according to the invention is provided that comprises an gene segment that is derived from an influenza virus that is recommended by WHO for vaccine purposes. In a preferred embodiment, the invention provides a nucleic acid comprising an influenza A gene segment and a T7 promotor or a complementary strand of said nucleic acid. Especially in a bidirectional system, it is preferred that a nucleic acid according to the invention is not comprising a T7 terminator. Because the polymerase is preferably expressed from a plasmid transfected together with the plasmids expressing the virus, the system provided herein is not restricted to a certain species. Although T7 polymerase-based reverse genetics systems are sometimes used for the rescue of non-segmented negative strand viruses, a reverse genetics system for the segmented influenza virus based on bacteriophage polymerase technology has never been successfully utilized before. One limiting factor in reverse genetics systems using T7 polymerase for transcribing the cDNA is sometimes sought to overcome by introducing G residues at the transcription start site to enhance the T7-polymerase driven transcription. This approach has been used in rescue of, e.g. RV, VSV and SV, however, Zobel el al (Virology. 1994 July; 202(1):477-9; Nucleic Acids Res. 1993 Aug. 11; 21(16):3607-14) specify that both the 5' and the 3' of an influenza A gene segment need to be precisely defined in order for the viral polymerase to function properly; therefore apparently leaving no space for additional nucleotide addition at transcription sites and teaching against introducing G residues at the transcription start site. Surprisingly, however, in a preferred embodiment of the invention, we provide a nucleic acid according to the invention having been provided with at least one additional guanine residue next to the T7 promotor, it is even preferred that two additional guanine residues are provided next to the T7 promotor. Also, the invention provides A Madin Darby Canine Kidney (MDCK) or Chicken Embryo Fibroblast (CEF) cell provided with T7 polymerase. In particular, the invention provides a cell provided with at least one nucleic acid according to the invention. The invention facilitates the use of a multi-plasmid system, such as a 17-plasmid, or a 12-plasmid or an 8-plasmid system, and, because the invention provides a cell with a nucleic acid according to the invention additionally provided with T7 polymerase, preferably expressed from a plasmid transfected together with one or more of the plasmids capable of expressing an influenza gene segment according to the invention, the system is not restricted to a certain species. It is herein also provided to use a cell according to the invention wherein said T7 polymerase comprises a nuclear localization signal. In a preferred embodiment, a cell as provided herein is a non-primate cell, thereby avoiding the introduction of primate DNA in cell material or vaccine derived from a nucleic acid or cell according to the invention. Preferably a MDCK cell or a CEF cell is used. It is an advantage of the invention that no helper virus is required for the reverse genetics system, all viral particles provided by the transfection comprise the desired nucleic acid and can be used without elaborate cloning procedures in a subsequent vaccine production system. The invention also provides for the first time a replicative viral particle comprising a nucleic acid according to the invention.

In U.S. Pat. No. 5,166,057, such a viral particle capable of replication has not been provided and other attempts to utilize the T7 system for the segmented influenza virus have until this invention also been fruitless. Cell culture compositions with virus titers of ~$10^4$ of the viral particle as provided herein can easily be obtained without virus replication in the transfected cell culture which can be boosted to >$10^7$ when the virus is allowed to replicate. It is particularly useful that replication of a particle according to the invention is achieved without a helper virus. Such a cell culture composition comprising a cell or material derived from a cell according to the invention or a virus or material derived from a viral particle according to the invention can advantageously be used for the production of a pharmaceutical composition directed at generating immunological protection against infection of a subject with an influenza virus. Certainly, such cells as provided herein have not been provided in U.S. Pat. No. 5,166,057. Thus, the invention also provides a method for producing a replicative influenza virus particle comprising culturing a cell with at least one nucleic acid according to the invention. It is preferred that the at least one nucleic acid used in said method comprises at least one, but preferably seven or eight influenza gene segments and a bacteriophage polymerase promotor or a complementary strand of said nucleic acid or acids. It is furthermore preferred that said segment does not comprise a bacteriophage polymerase terminator, whereby advantageously such a segment has been provided with at least one additional guanine residue next to the promoter, or has been provided with two additional guanine residues next to the promoter. Preferably, said segments are derived from an influenza virus that is recommended by WHO for vaccine purposes, for example an influenza A gene segment. Finally, the invention provides a replicative influenza virus particle obtainable with the method disclosed above. Therewith the invention also provides a method for generating immunological protection against infection of a subject with an influenza virus comprising providing a subject in need thereof with a composition as provided herein. Such compositions are preferably formulated as a vaccine, i.e. by admixing viral particles, or viral proteins derived from such particles (subunit-vaccines) with an appropriate pharmaceutical carrier such as a salt solution or adjuvant (e.g. an aluminum salt or other excipient commonly used)

FIGURE LEGENDS

FIG. 1 Constructs used for the T7pol-based reverse genetics system. See text for details on cloning strategies.

Figure 2:
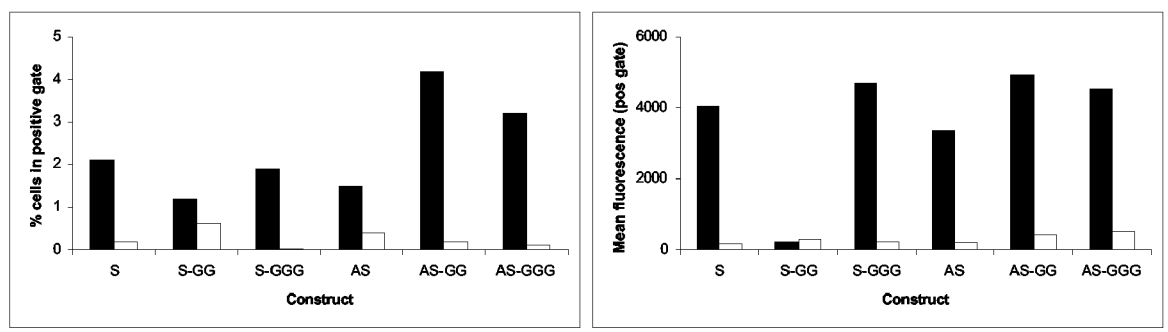

FIG. 2 FACS analysis of 293T cells transfected with constructs encoding GFP minigenomes (0.6 μg), T7pol (0.6 μg) and influenza A virus polymerase genes (each 1 μg). Left panel: % GFP positive cells 30 hours after transfection. Right panel: level of GFP expression (mean fluorescence) in the GFP positive fraction. On the X-axis, the transfected GFP minigenome constructs in either sense (S) or antisense (AS) orientation are shown, with the number of additional G nucleotides indicated. Black bars indicate cotransfections with all 4 components of the influenza A virus polymerase complex (PB2, PB1, PA and NP), white bars indicate control transfections from which the pHMG-NP construct was omitted.

Figure 3:
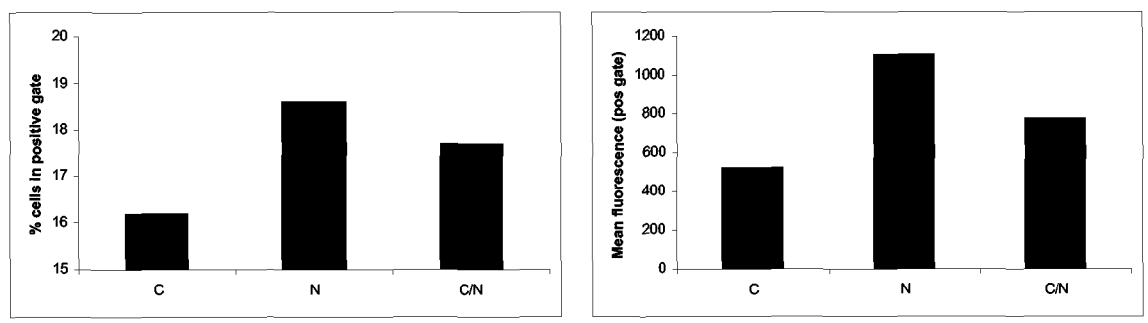

FIG. 3 FACS analysis of 293T cells transfected with 0.6 μg of the antisense GFP minigenomes with 2 additional G residues, 4 μg of influenza A virus polymerase constructs, and 0.6 μg of either a wild type T7pol (C), a T7pol containing a nuclear localization signal (N), or both constructs in a 1:1 ratio (C/N). Left panel: % GFP positive cells 30 hours after transfection. Right panel: level of GFP expression (mean fluorescence) in the GFP positive fraction.

Figure 4:
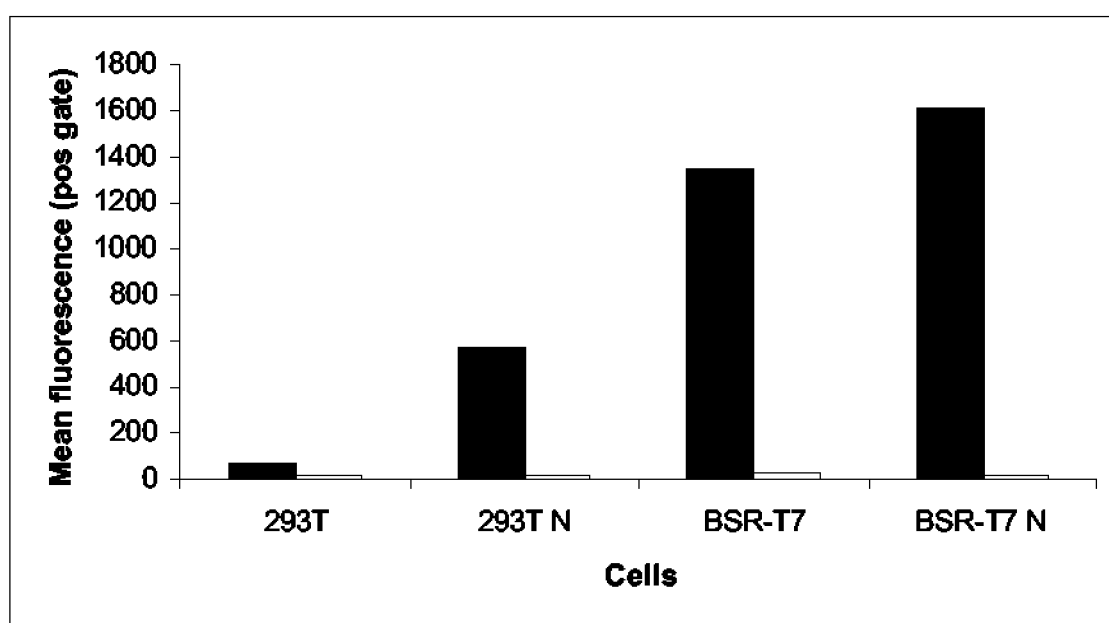

FIG. 4 FACS analysis of 293T or BSR-T7 cells transfected with 0.6 μg of the construct encoding the antisense GFP minigenome with 2 additional G residues and 4 μg of the influenza A virus polymerase constructs. The level of GFP expression (mean fluorescence) in the GFP positive fraction of cells is shown. Cells were transfected with or without a plasmid expressing T7pol containing a nuclear localization signal (293T vs. 293T N or BSR-T7 vs. BSR-T7 N). Black bars indicate cotransfections with all 4 components of the influenza A virus polymerase complex (PB2, PB1, PA and NP), white bars indicate control transfections from which the pHMG-NP construct was omitted.

Figure 5:
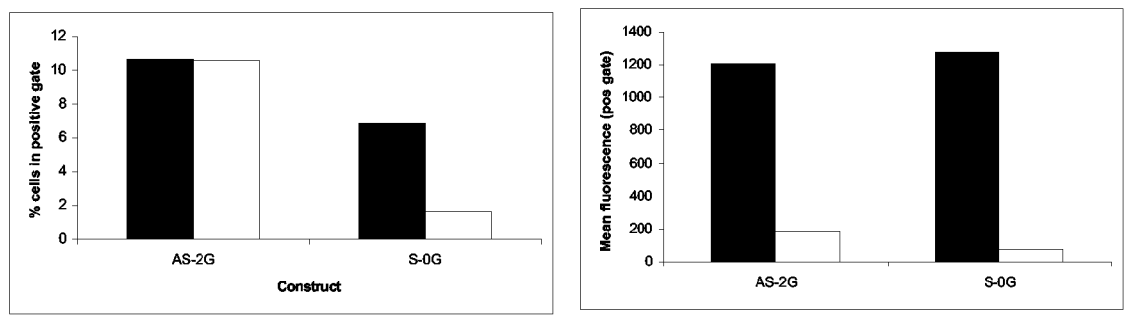

FIG. 5 FACS analysis of 293T cells transfected with 0.6 μg constructs encoding the antisense GFP minigenome with 2 additional G residues (AS-2G) or sense GFP minigenome (S-0G), and 0.6 μg of a plasmid expressing T7pol with a nuclear localization signal and 4 μg of plasmids expressing the influenza A virus polymerase genes. Left panel: % GFP positive cells 30 hours after transfection. Right panel: level of GFP expression (mean fluorescence) in the GFP positive fraction. Black bars indicate cotransfections with all 4 components of the influenza A virus polymerase complex (PB2, PB1, PA and NP), white bars indicate control transfections from which the pHMG-NP construct was omitted.

Figure 6:
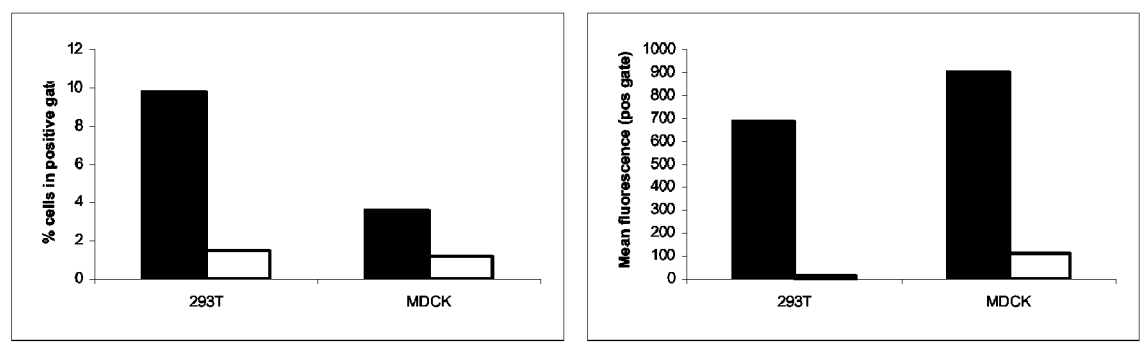

FIG. 6 FACS analysis of 293T and MDCK cells transfected with 0.6 μg constructs encoding the antisense GFP minigenome with 2 additional G residues (AS-2G), 0.6 μg of a plasmid expressing T7pol with a nuclear localization signal and 4 μg of plasmids expressing the influenza A virus polymerase genes. Left panel: % GFP positive cells 30 hours after transfection. Right panel: level of GFP expression (mean fluorescence) in the GFP positive fraction. Black bars indicate cotransfections with all 4 components of the influenza A virus polymerase complex (PB2, PB1, PA and NP), white bars indicate control transfections from which the pHMG-NP construct was omitted.

DETAILED DESCRIPTION

Example 1

Generation of Recombinant Influenza A Virus Using a T7 RNA Polymerase Based Reverse Genetics System
Introduction For a long time, the fundamental research of influenza A viruses has been hampered by the lack of availability of efficient reverse genetics systems. Although the earliest reverse genetics techniques for negative stranded RNA viruses were in fact developed for influenza A virus (7, 18), the rescue of this virus exclusively from recombinant DNA was achieved only recently (9, 20).

Influenza A virus is a negative strand RNA virus. During the virus replication cycle, three types of RNA are produced: negative sense genomic viral RNA (vRNA), positive sense RNA complementary to the genomic RNA (cRNA) and positive sense messenger RNA (mRNA). Whereas the vRNA and cRNA contain essentially unmodified ends, the mRNA is capped and has a poly(A) tail (16).

RNA polymerase I (PolI) is a nucleolar enzyme that transcribes ribosomal RNA (rRNA) and is abundantly expressed in growing cells. Like vRNA, rRNA has no cap and no poly (A)tail (23). Hobom and colleagues (19, 21, 29) successfully produced artificial influenza virus vRNA-like segments with precise 5' and 3' ends using PolI. Transcription of cDNA cloned in the context of a PolI promoter-terminator cassette allowed the generation of vRNA-like molecules with correct 5' and 3' ends (29). Subsequent studies which involved helper influenza virus demonstrated that these genomic vRNA molecules could be recognized and replicated by the influenza virus polymerase complex and packaged into progeny influenza viruses. This system allowed the generation of influenza viruses containing mutations in one of the viral gene segments or an additional gene segment, thus allowing studies of viral genes and their products. As the result of the use of helper virus, selection of transfectant virus was required, this is rather cumbersome.

Neumann et al. designed a PolI system for the recovery of influenza A viruses entirely from cloned cDNA (20). cDNAs encoding full-length vRNAs of the influenza A virus were cloned between the human PolI promoter and the mouse PolI terminator. In principle, transfection of these eight plasmids into eukaryotic cells should result in the synthesis of all eight influenza vRNAs. Human embryonic kidney cells (293T) were cotransfected with these eight vRNA expression plasmids and plasmids expressing the viral nucleoprotein and the polymerase proteins PB2, PB1 and PA from an RNA polymerase II (PolII) promoter. The vRNAs synthesized by the cellular PolI were packaged into RNPs and amounts greater than $1 \times 10^3$ plaque-forming units of infectious virus per ml (pfu/ml) of supernatant were recovered. Cotransfection with plasmids expressing the remaining viral structural proteins led to a substantial increase in virus production, namely $3 \times 10^4$ to $5 \times 10^7$ pfu/ml (20). Fodor et al. reported a similar system for the recovery of influenza A virus (9). This system depended on eight plasmids encoding all eight vRNA cDNAs, flanked by a human PolI promoter but which contained a hepatitis δ virus ribozyme (HδVrib) sequence rather than a PolI terminator sequence. These plasmids were cotransfected into Vero cells with four plasmids expressing the PB1, PB2, PA and NP proteins from an adenovirus type 2 major late promoter. Using equal amounts of each of the expression plasmids, Fodor et al. reported a rescue rate of 1 to 2 infectious viral particles from $10^6$ transfected cells (9). We had designed a similar reverse genetic system to produce recombinant influenza virus A/PR/8/34. We concluded that virus titers of $\sim 10^4$ can be obtained without virus replication in the transfected cell culture which can be boosted to $>10^7$ when the virus is allowed to replicate (4). Since these PolI-driven systems required the cotransfection of 12-16 plasmids, the use of cell lines that can be transfected with high efficiencies were necessary for efficient production of recombinant virus.

Subsequently, Hoffmann et al. developed a bidirectional PolI-PolII transcription system for the generation of influenza A virus from only eight plasmids (12). In this bidirectional system, the vRNA cDNA was inserted between the human PolI promoter and the minimal mouse PolI terminator sequences. This entire cassette was inserted between a Pol promoter and a polyadenylation site. This allowed the transcription of vRNA and mRNA from the PolI and PolII promoters respectively, from a single construct. Cotransfection of eight PolI-PolII plasmids, each encoding one of the influenza A virus gene segments, in 293T cells cocultured with Madin Darby Canine Kidney (MDCK) cells resulted in the recovery of infectious influenza A virus, with yields up to $2 \times 10^7$ pfu/ml supernatant (12). The use of one template for the synthesis of both mRNA and vRNA reduced the number of plasmids required for virus generation. The efficiency of virus generation in this system was reported to be similar to that of the unidirectional (12-16 plasmid) PolI system.

Whereas PolII promoters are often compatible with the transcription machinery from different species, transcription from PolI promoters exhibits stringent, though not absolute, species specificity. This species-specificity is conferred by the interaction of transcription factors with the promoter and, to a lesser extent, in the protein-protein interactions between these factors (23).

The species-specificity of the PolI-based reverse genetics systems forms a major disadvantage. The reverse genetics systems described above employed a human PolI promoter, limiting the production of recombinant virus to cells of primate origin, such as 293T cells or Vero cells. While PolI promoters have been characterized for several species including human, mouse, rat, and pig (8, 14, 17), they remain unknown for many others. Canine and avian cells are routinely used for influenza A virus research and vaccine production, but the canine and avian PolI promoters have not yet been described. To improve the flexibility of influenza virus reverse genetics technology, we sought to develop a universal reverse genetics system. We have chosen to design a system based on the expression of the gene segments of influenza A virus under the control of a bacteriophage T7 RNA polymerase promoter (pT7). Because the bacteriophage T7 RNA polymerase (T7pol) can be supplied to cells by transfection or through the use of stably modified cell lines, this system is not restricted to cells from a particular species.

T7pol-based reverse genetics systems are used for the rescue of non-segmented negative strand viruses. Schnell et al. were the first to rescue a non-segmented negative strand virus solely from cloned cDNA (27). A cDNA clone was made encoding the full-length anti-genomic RNA of the rabies virus (RV). This cDNA was flanked by pT7 and a HδVrib sequence next to a T7pol terminator sequence (tT7). Following transcription by T7pol, a precise 3' end of the genome is generated by autolytic cleavage of the HδVrib sequence at the 3' end. This plasmid was cotransfected with expression plasmids encoding the viral N protein and the polymerase proteins L and P under the control of pT7 into cells expressing the T7pol. This procedure led to the rescue of recombinant RV, but only from approximately 1 of $2\times10^7$ transfected cells (27). Since then, similar systems have been described for the *Paramyxoviridae*, *Rhabdoviridae* and *Filoviridae* families of nonsegmented NSV (10).

For successful recovery of non-segmented negative strand viruses from cDNA, very often positive-sense antigenomic RNA (cRNA) is produced rather than the negative-sense vRNA. It is thought that the simultaneous presence of naked negative-sense vRNA and positive sense mRNA encoding the viral proteins will result in hybridization, preventing the assembly of the genome into ribonucleoprotein complexes (RNPs) (27). Negative strand viruses normally do not encounter this problem since they always keep their genome in the RNP form, which prevents hybridization. Recovery of Sendai virus (15), human parainfluenza virus type 3 (6) and human metapneumovirus (11) has been reported with cDNA encoding negative-sense genomic RNA; however, the efficiencies were significantly lower than results with positive-sense RNA. This principle has also been applied for the rescue of recombinant influenza virus. Hoffmann et al. (13) also determined the efficiency of recombinant influenza virus production from antigenomic positive-sense RNA. In contrast to non-segmented and segmented negative strand viruses replicating solely in the cytoplasm, influenza A virus could be rescued from both genomic and antigenomic vectors with similar efficiencies.

One limiting factor in virus rescue systems using pT7 is that residues at the +1 to +3 positions can affect transcription. It was observed that transcription of a cDNA can be increased by the introduction of 2 or 3 G residues directly downstream of pT7 (22). This observation has been applied for the rescue of, e.g. recombinant RV (27), vesicular stomatitis virus (28), respiratory syncytial virus (3), and human metapneumovirus (11). Apparently, for these viruses, the additional G residues at one of the genomic termini did not affect virus replication but had a positive effect on the T7pol-driven transcription.

T7pol-based systems have been used extensively for influenza virus reverse genetics studies (18), but plasmid-based production of recombinant influenza virus has not been described to date. Here we describe such a T7pol based reverse genetics system for the production of recombinant influenza virus for the first time.

Materials and Methods

Cells and Viruses

Madin-Darby Canine kidney (MDCK) cells were cultured in EMEM (BioWhittaker) supplemented with 10% FCS, 100 IU/ml penicillin, 100 µg/ml streptomycin, 2 mM glutamine, 1.5 mg/ml sodiumbicarbonate, 10 mM Hepes and non-essential amino acids. 293T cells were cultured in DMEM (BioWhittaker) supplemented with 10% FCS, 100 IU/ml penicillin, 100 µg/ml streptomycin, 2 mM glutamine, 1 mM sodiumpyruvate and non-essential amino acids. BSR-T7 cells, a baby hamster kidney cell line stably expressing T7 RNA polymerase (2). BSR-T7 cells were grown in DMEM supplemented with 10% FCS, 100 IU/ml penicillin, 100 µg/ml streptomycin, 2 mM glutamine, 1 mM sodiumpyruvate and 0.5 mg/ml G418 (Life Technologies, Breda, The Netherlands). Influenza virus A/PR/8/34, being adapted for replication in embryonated chicken eggs and may not replicate optimally in mammalian cell cultures, was passaged seven times at a low multiplicity of infection in MDCK cells grown in Episerf media (Gibco BRL) supplemented with 10 IU/ml penicillin and 10 µg/ml streptomycin. After the seventh passage, virus titers of $10^8$ TCID$_{50}$/ml were obtained routinely.

Transfection of 293T Cells

Transient calcium phosphate-mediated transfections of 293T cells were performed essentially as described (24). Cells were plated the day before transfection in gelatinized 100 mm diameter culture dishes to obtain 50 percent confluent monolayers. After overnight transfection the transfection medium was replaced with fresh medium supplemented with 2% FCS for virus production or 10% FCS for all other transfections. Cells were incubated for 30 to 72 hours, after which supernatants were harvested and cells were analyzed for fluorescence if appropriate. Plasmid pEGFP-N1 (Clontech, BD Biosciences, Amsterdam, The Netherlands) was transfected in parallel in all experiments and the percentage of fluorescent cells was measured in a FACSCalibur (Becton Dickinson) flow cytometer, confirming that the transfection efficiency ranged from 95-100 percent. Virus-containing supernatants were cleared by centrifugation for 10 minutes at 300×g. Virus titers in the supernatant were determined either directly or upon storage at 4° C. for less than one week, or at −80° C. for longer than one week.

Transfection of MDCK Cells

Transient transfection of MDCK cells was performed essentially as described previously (1). Briefly, 240 µl of Optimem I medium (GibcoBRL) was added to 10 µl of Lipofectamin 2000 and incubated at room temperature for 5 minutes. To this mixture, the intended amount of DNA, adjusted to a volume of 50 µl using Optimem I media was added. This mixture was incubated at room temperature for 20 minutes. After incubation, 200 µl MDCK culture medium (see above) without penicillin and streptomycin was added and this mixture was added to $1\times10^6$ MDCK cells in suspension in a 6-well plate. After 5 hours incubation, cells were washed twice with PBS and cultured in 2 ml MDCK culture medium without penicillin and streptomycin. This medium was replaced with MDCK culture medium containing 2% FCS after overnight incubation.

Transfection of BSR-T7 Cells

For transient transfection of BSR-T7 cells, 400.000 cells were plated in a 6-wells culture dish a day before transfection to obtain 50-70% confluent monolayers. Serum free DMEM (240 μl) was added to 10 μl of Lipofectamin 2000 and incubated for 4 minutes at room temperature. To this mixture, DNA adjusted to 50 μl with serum free DMEM was added, and incubated at room temperature for 20 minutes. Before transfection, medium was replaced with 2 ml of serum free DMEM. After incubation, the transfection mixture was added drop wise to the cells and incubated for 5 hours at 37° C. After transfection, cells were washed with PBS once and 2 ml of DMEM supplemented with 2% FCS for virus production or with 10% FCS for FACS analyses was added.

Plasmids

Eukaryotic expression vectors encoding T7pol (pAR3126 and pAR3132) were used. Whereas plasmid pAR3126 encodes a wild type T7pol, plasmid pAR3132 expresses a T7pol containing a nuclear localization signal (NLS), that effectively targets the T7pol to the cell nucleus (5). Eukaryotic expression plasmids from which the influenza A virus polymerase proteins are expressed employing a mouse hydroxy-methylglutaryl-coenzyme A reductase promoter, pHMG-PB1, pHMG-PB2, pHMG-PA and pHMG-NP (25).

The HδVrib of pPolI-CAT-RT (25) was amplified by PCR and cloned in the XbaI-BamHI sites of pSP72. A tT7 sequence, digested with BamHI-EcoRV, was cloned in the BamHI-HpaI sites of pSP72-HδVrib, resulting in pSP72-HδVrib-tT7 (MS24). An oligonucleotide encoding the pT7 was ligated in the NdeI-XbaI sites of pSP72-HδVrib-tT7 in the appropriate context to introduced BbsI sites, resulting in vector pSP72-pT7-HδVrib-tT7 (MS25, FIG. 1). A green fluorescent protein (GFP) open reading frame flanked by NCRs from segment 5 of influenza virus A/PR/8/34, was cloned in the BbsI sites of pSP72-pT7-HδVrib-tT7, using pSP-Hu-GFP-Mu (4) as a template. This GFP minigenome was cloned both in the sense and antisense orientations, and contained either 0/2/3 additional G residues directly downstream of pT7 (FIG. 1).

To clone the gene segments of influenza virus A/PR/8/34 in pSP72-pT7-HδVrib-tT7, the bidirectional influenza virus A/PR/8/34 constructs described by de Wit et al. (4) were used as a template for PCR (the fourth 3' nucleotide was in correspondence to the influenza virus A/PR/8/34 sequences reported at the National Influenza sequence Database). Primers containing an AarI restriction site were used for cloning segment 1,2,3,4,6,7,8 and blunt end ligation was used for segment 5; the gene segments were cloned in the BbsI sites in an antisense orientation containing 2 additional G residues after pT7.

A bidirectional vector pSP72-pT7-HδVrib-tT7-pCMV (MS65, FIG. 1) was produced by cloning a CMV promoter (PCMV) downstream of tT7 to allow production of mRNA from the corresponding gene segments. pCMV was amplified by PCR using primers containing AseI restriction sites. pSP72-pT7-HδVrib-tT7 was partially digested with AseI and pCMV was ligated downstream from the tT7 in the appropriate direction for production of mRNA from the gene segment.

Again, the influenza virus A/PR/8/34 segments were cloned to obtain each of the bidirectional T7pol-driven influenza virus A/PR/8/34 constructs.

We also generated a set of bidirectional vectors from which tT7 was deleted. This was done by digesting pSP72-pT7-HδVrib-tT7-pCMV with BamHI-BpeEI, treatment with klenow enzyme, and relegation, to generate pSP72-pT7-HδVrib-pCMV (MS90, FIG. 1). Again, the influenza virus A/PR/8/34 segments were cloned to obtain each of the bidirectional T7pol-driven influenza virus A/PR/8/34 constructs.

All plasmids were sequenced using a Big Dye Terminator v3.1 Cycle Sequencing kit (Applied Biosystems) and a 3100 Genetic Analyser (Applied Biosystems), according to the instructions of the manufacturer.

Production of Recombinant Virus with the T7pol-Based System

293 T cells were transfected, as described above, with 5 μg from each of the unidirectional plasmids containing a gene segment of PR/8/34, 5 μg of the expression plasmids HMG-PB2, HMG-PB1, HMG-PA, HMG-NP each and 15 μg of pAR3132. Alternatively, we transfected 5 μg from each of the bidirectional plasmids containing a gene segment of PR/8/34 and 15 μg of pAR3132. Supernatants were harvested 72 hours after transfection and 1 ml was used to infect a confluent monolayer of MDCK cells.

Virus Infections and Titrations

Prior to inoculation, MDCK cells were washed twice with PBS, and 1 ml of 293T supernatant was used to inoculate a confluent monolayer of MDCK cells in a 6-well plate; 40 μg of trypsin (2.5%, Bio Whittaker) was added during infection. Plates were stored at 37° C. for 1 hour and washed twice with PBS, after which 2 ml of EMEM (BioWhittaker) supplemented with 4% BSA, 100 IU/ml penicillin, 100 μg/ml streptomycin, 2 mM glutamine, 1.5 mg/ml sodiumbicarbonate, 10 mM Hepes, non-essential amino acids and 20 μg/ml trypsin (infection medium) was added. At 3 days post infection, the supernatants of the cultures were harvested and tested for HA activity as an indicator for infection of the cells. Virus titrations were performed as described previously (26). Briefly, ten-fold serial dilutions of the transfected cell supernatants were prepared in infection medium. Prior to inoculation, the cells were washed twice with PBS. 100 μl of the diluted culture supernatants was used to inoculate a confluent monolayer of MDCK cells in 96 wells plates. After 1 h at 37° C. the cells were washed again with PBS and 200 μl of fresh infection medium was added to each well. At 3 days post infection, the supernatants of the cultures were tested for HA activity as an indicator for infection of the cells in individual wells. The infectious titers were calculated from 10 replicates according to the method of Spearman-Karber (26).

Results

GFP minigenome assays with a unidirectional T7pol-based reverse genetics system A unidirectional vector containing pT7, HδVrib and tT7 was constructed. A GFP open reading frame flanked by the non coding regions (NCRs) of segment 5 of influenza virus A/PR/8/34 was cloned in pSP72-pT7-HδVrib-tT7 in the sense (S) and antisense (AS) orientation with 0, 2 or 3 additional G residues (FIG. 1 and appendices 2 and 3). These constructs were named S-0G, S-2G, S-3G, AS-0G, AS-2G and AS-3G respectively. We tested which of these options resulted in the best performance.

We transfected 293T cells with one of the GFP minigenomes (S-0G, S-2G, S-3G, AS-0G, AS-2G, AS-3G), a T7pol expression plasmid (pAR3132), and four plasmids expressing the PB2, PB1, PA and NP proteins (pHMG-PB2, pHMG-PB1, pHMG-PA, pHMG-NP). As controls, we performed the same transfections from which pHMG-NP was omitted, which should result in the lack of replication of the GFP minigenome. At 30 hours after transfection the cells were analyzed for fluorescence in a FACSCalibur.

The results are depicted in FIG. 2. From the left panel it can be seen that the highest proportion of GFP positive cells were observed upon transfection of the GFP minigenome in the antisense orientation, with two additional G residues.

The other GFP minigenome constructs also yielded a proportion of GFP positive cells, but somewhat smaller. When the mean fluorescence of the GFP positive cells was compared (FIG. 2, right panel), again the GFP minigenome in the antisense orientation with two additional G residues displayed the best performance. In this experiment, the GFP minigenome in the sense orientation with two additional G residues displayed the poorest performance, and other constructs were intermediate.

While we observed some variation with respect to the proportion of GFP-expressing cells and levels of GFP expression between the different GFP minigenome plasmids from experiment to experiment (data not shown), the GFP minigenome in the antisense orientation with two additional G residues in general performed best, and this construct was thus selected for subsequent experiments.

Nuclear Versus Cytoplasmic T7pol Expression

One problem that we potentially needed to solve was the expression of T7pol. For paramyxovirus reverse genetics, a T7pol expressed primarily in the cell cytoplasm is used, which is desirable since paramyxovirus replication also takes place in the cytoplasm. Influenza viruses replicate in the cell nucleus, and expression of T7pol in the cytoplasm may thus not be the best option. We thus wished to compare the level of GFP expression when either a cytoplasmic version of T7pol was used (plasmid AR3126), or a T7pol containing a nuclear localization signal (NLS, plasmid pAR3132).

The results of this experiment are shown in FIG. 3. When a wild type T7pol expression plasmid was used, the mean GFP fluorescence in the positive cells was 521. The level of GFP expression could be enhanced significantly by using a T7pol that contained a nuclear localization signal (mean fluorescence 1106). When both the T7pol constructs with and without the nuclear localization signal were combined (1:1 ratio, keeping the total amount of transfected plasmid unchanged), an intermediate level of GFP expression was observed (mean fluorescence 775). In numerous independent experiments, using a wide variety of GFP minigenome plasmids, these results were reproducible; a 2 to 10-fold increase in GFP expression was observed when a nuclear version of T7pol was used (data not shown). Thus, in subsequent experiments, we have made use of the T7pol containing a nuclear localization signal.

Transient Versus Stable T7pol Expression

For several paramyxovirus reverse genetics systems, the T7pol is not supplied by plasmid transfection but through the use of a cell line that allows the stable expression of T7pol. For this purpose, baby hamster kidney cells (BSR-T7) are available. We tested whether BSR-T7 cells could be used for the transcription of the influenza virus GFP minigenome which could subsequently be replicated by the influenza virus polymerase complex, resulting in GFP expression (FIG. 4).

As can be seen in FIG. 4, high GFP fluorescence in 293T cells is strongly dependent of the expression of the T7pol. In BSR-T7 cells, relatively high levels of GFP expression were observed upon cotransfection of the GFP minigenome with the influenza virus polymerase complex, in contrast to transfections from which the pHMG-NP plasmid was omitted. Upon the addition of a plasmid expressing a nuclear version of T7pol, GFP expression was found to be even higher. The relatively high levels of GFP expression in BSR-T7 cells suggest that the stable expression of T7pol is more efficient than transient expression by transfection. However, the experiment in which nuclear T7pol was provided by transfection suggests that for influenza virus reverse genetics, a stable cell line expressing a nuclear T7pol rather than the wild type T7pol would be even more efficient.

Production of Recombinant Virus with a Unidirectional T7pol-based Reverse Genetics System Next, the gene segments of influenza virus A/PR/8/34 were cloned in vector pSP72-pT7-HδVrib-tT7 for the generation of recombinant influenza virus A/PR/8/34.

We transfected 293T cells with the eight constructs encoding the gene segments of influenza virus A/PR/8/34, pT7pol (pAR3132), pHMG-PB1, pHMG-PB2, pHMG-PA and pHMG-NP. After transfection, trypsin was added to the medium to allow replication of the produced viruses. At 72 h after transfection, supernatants were harvested and used to inoculate MDCK cells. At 3 days after inoculation, a HA-test was performed on the supernatant of these MDCK cells as an indication of virus replication. The HA-test was positive. Subsequently, the virus titer of the 293T and MDCK supernatant was determined. The virus titer in the 293T supernatant was shown to be $1.6 \times 10^1$ TCID$_{50}$/ml; the virus titer in the MDCK supernatant was shown to be $2.0 \times 10^7$ TCID$_{50}$/ml. Somewhat lower virus titers in 293T cells and MDCK cells were obtained when trypsin was not added to 293T cells after transfection (data not shown). This thus represents the first plasmid-only recombinant influenza A virus rescue that did not employ a PolI promoter.

A Bidirectional T7 System

We next wished to develop a bi-directional reverse genetics system under the control of the pT7. A plasmid vector was produced by cloning pCMV in pSP72-pT7-HδVrib-tT7, resulting in vector pSP72-pT7-HδVrib-tT7-pCMV (FIG. 1). A GFP open reading frame flanked by the non-coding regions (NCRs) of segment 5 of influenza virus A/PR/8/34 was cloned in pSP72-pT7-HδVrib-tT7-pCMV in antisense orientation with 2 additional G residues. Because we anticipated that this plasmid would give rise to GFP expression without the need for minigenome replication by the influenza virus polymerase complex (PCMV is in the sense orientation with respect to the minigenome), we also made a similar construct containing the minigenome (0 G residues) in the sense orientation with respect to pT7 (hence antisense with respect to PCMV). The minigenome plasmids were transfected in 293T cells along with plasmids expressing the nuclear T7pol and pHMG-PB1, pHMG-PB2, pHMG-PA and pHMG-NP. Cells were analyzed by FACS after 30 hours (FIG. 5).

Transfection of the sense GFP minigenome (S-0G) with an incomplete influenza virus polymerase complex resulted in very few GFP positive cells (FIG. 5, left panel) with very low GFP expression (FIG. 5, right panel). In the presence of the complete influenza virus polymerase complex, ~7% of cells were GFP positive with a mean fluorescence of ~1200. Using the antisense GFP minigenome plasmid, a relatively large proportion of the cells (~10%) expressed GFP in the absence of a complete influenza virus polymerase complex, but only at low levels (mean GFP fluorescence 182). Upon cotransfection of the complete influenza virus polymerase complex, the proportion of cells expressing GFP did not increase, whereas the level of GFP expression per cell increased significantly (mean GFP fluorescence 1205). Thus, from this experiment we could conclude that the bidirectional expression vector was functional; we observed low levels of GFP expression without the need for the influenza virus polymerase complex, as a result of production of GFP mRNA from the pCMV. Of note, this was confirmed by transfection of 293T cells with the AS-2G GFP minigenome plasmid alone, resulting in similar levels of GFP expression (~19% of cells expressing at a mean fluorescence of 128, data not shown). In addition, we observed increased levels of GFP expression in the presence of the influenza virus polymerase complex as a result of replication of the minigenome transcribed from pT7. Thus, the bidirectional pT7-pCMV expression plasmid was functional.

Production of Recombinant Virus with a Bidirectional T7pol-based Reverse Genetics System Next, the gene segments of influenza virus A/PR/8/34 were cloned in vector pSP72-pT7-HδVrib-tT7-pCMV for the generation of recombinant influenza virus A/PR/8/34. We transfected 293T cells with the eight constructs encoding the gene segments of influenza virus A/PR/8/34 and pT7pol (pAR3132). After transfection, trypsin was added to the medium to allow replication of the produced viruses. At 72 h after transfection, supernatants were harvested and used to inoculate MDCK cells. At 3 days after inoculation, a HA-test was performed on the supernatant of these MDCK cells as an indication of virus replication. The HA-test was negative, indicating that no recombinant virus was recovered.

From minigenome reporter assays using the bidirectional vectors to express the PB2, PB1, PA and NP genes, we obtained evidence that protein expression from these plasmids was very low (data not shown). We hypothesized that the tT7 sequence was interfering with transcription form pCMV, resulting in low production of the encoded genes. We thus generated a new bidirectional plasmid, from which the tT7 sequence was removed (pSP72-pT7-HδVrib-pCMV). The gene segments of influenza virus A/PR/8/34 were cloned in vector pSP72-pT7-HδVrib-pCMV for the generation of recombinant influenza virus A/PR/8/34. In initial attempts, again no recombinant virus was produced. However, upon some optimization of the amount of plasmids used for transfection we successfully produced recombinant virus. The amounts of plasmids used for this experiment were 10 μg each of the constructs encoding PB2, PB1, PA and HA, and 5 μg each of the constructs encoding NP, NA, MA, and NS. While the recombinant virus titers in the 293T cells were undetectable, subsequent inoculation of MDCK cells resulted in a virus with an initial titer of $1.3 \times 10^5$ TCID50/ml.

The T7pol System in MDCK Cells

To provide further evidence for the universal nature of the reverse genetics system based on T7pol, we tested the replication of the GFP minigenome in MDCK cells rather than 293T cells. Although the experiments with BSR-T7 cells already provided evidence that the T7pol reverse genetics system works in cells of non-primate origin (FIG. 4), MDCK are more widely used for influenza virus research and vaccine production.

As can be seen in FIG. 6, the T7pol-based reverse genetics system was found to be functional in MDCK cells. Combined with the results in BSR-T7 cells (FIG. 4), these experiments indicate that the T7pol reverse genetics system indeed represents a "universal" system, applicable to wide variety of cell types. From this experiment, it can also be concluded that production of recombinant influenza viruses from non-primate cells is now possible.

Here we have shown, for the first time, the production of recombinant influenza A virus A/PR/8/34 (MDCK-adapted NIBSC strain) using a T7pol-based system in 293T cells. However, there are no assumptions that limit the use of these methods to influenza A virus A/PR/8/34; they can be applied to all influenza viruses of types A, B and C as well as other segmented negative stranded RNA viruses. There are also no assumptions that limit the use of these methods to 293T cells, BSR-T7 cells and MDCK cells; the T7pol can be supplied by, for instance, transfection of a wide range of cell lines in which recombinant virus could then be produced.

There is also significant flexibility with respect to the plasmid vectors for this T7pol-based reverse genetics technology, and the elements that they contain. Here, we used the RNA polymerase of bacteriophage T7 to produce vRNA or cRNA-like RNA molecules but various other RNA polymerases such as the bacteriophage SP6 RNA polymerase could be used also. In the experiments shown here, the T7 RNA polymerase was modified to contain the nuclear localization signal of the SV40 large T antigen, but RNA polymerases may be modified using a variety of other nuclear targeting signals (e.g. those of the hnRNP K protein). We here employed the ribozyme sequence of the hepatitis delta virus but other ribozyme sequences have been described that could be used alternatively. Finally, the system described here is not dependent on the use of influenza virus polymerase protein expression vectors based on the mouse hydroxy-methylglutaryl-coenzyme A reductase promoter (pHMG constucts); polymerase proteins from a wide range of influenza viruses could be used, and expressed using a wide range of expression vectors.

References

1. Basler, C. F., X. Wang, E. Muhlberger, V. Volchkov, J. Paragas, H. D. Klenk, A. Garcia-Sastre, and P. Palese. 2000. The Ebola virus VP35 protein functions as a type I IFN antagonist. Proc Natl Acad Sci USA 97:12289-94.
2. Buchholz, U. J., S. Finke, and K. K. Conzelmann. 1999. Generation of bovine respiratory syncytial virus (BRSV) from cDNA: BRSV NS2 is not essential for virus replication in tissue culture, and the human RSV leader region acts as a functional BRSV genome promoter. J Virol 73:251-9.
3. Collins, P. L., M. G. Hill, E. Camargo, H. Grosfeld, R. M. Chanock, and B. R. Murphy. 1995. Production of infectious human respiratory syncytial virus from cloned cDNA confirms an essential role for the transcription elongation factor from the 5' proximal open reading frame of the M2 mRNA in gene expression and provides a capability for vaccine development. Proc Natl Acad Sci USA 92:11563-7.
4. de Wit, E., M. I. Spronken, T. M. Bestebroer, G. F. Rimmelzwaan, A. D. Osterhaus, and R. A. Fouchier. 2004. Efficient generation and growth of influenza virus A/PR/8/34 from eight cDNA fragments. Virus Res 103:155-61.
5. Dunn, J. J., B. Krippl, K. E. Bernstein, H. Westphal, and F. W. Studier. 1988. Targeting bacteriophage T7 RNA polymerase to the mammalian cell nucleus. Gene 68:259-266.
6. Durbin, A. P., S. L. Hall, J. W. Siew, S. S. Whitehead, P. L. Collins, and B. R. Murphy. 1997. Recovery of infectious human parainfluenza virus type 3 from cDNA. Virology 235:323-32.
7. Enami, M., W. Luytjes, M. Krystal, and P. Palese. 1990. Introduction of site-specific mutations into the genome of influenza virus. Proc Natl Acad Sci USA 87:3802-5.
8. Financsek, I., K. Mizumoto, Y. Mishima, and M. Muramatsu. 1982. Human ribosomal RNA gene: nucleotide sequence of the transcription initiation region and comparison of three mammalian genes. Proc Natl Acad Sci USA 79:3092-6.
9. Fodor, E., L. Devenish, O. G. Engelhardt, P. Palese, G. G. Brownlee, and A. Garcia-sastre. 1999. Rescue of influenza A virus from recombinant DNA. J Virol 73:9679-9682.
10. Garcia-Sastre, A. 1998. Negative-strand RNA viruses: applications to biotechnology. Trends Biotechnol 16:230-5.
11. Herfst, S., M. de Graaf, J. H. Schickli, R. S. Tang, J. Kaur, C. F. Yang, R. R. Spaete, A. A. Haller, B. G. van den Hoogen, A. D. Osterhaus, and R. A. Fouchier. 2004.

Recovery of human metapneumovirus genetic lineages a and B from cloned cDNA. J Virol 78:8264-70.
12. Hoffmann, E., G. Neumann, Y. Kawaoka, G. Hobom, and R. G. Webster. 2000. A DNA transfection system for generation of influenza A virus from eight plasmids. Proc Natl Acad Sci USA 97:6108-13.
13. Hoffmann, E., and R. G. Webster. 2000. Unidirectional RNA polymerase I-polymerase II transcription system for the generation of influenza A virus from eight plasmids. J Gen Virol 81:2843-7.
14. Ishikawa, Y., G. Safrany, K. Hisatake, N. Tanaka, Y. Maeda, H. Kato, R. Kominami, and M. Muramatsu. 1991. Structure of the core promoter of human and mouse ribosomal RNA gene. Asymmetry of species-specific transcription. J Mol Biol 218:55-67.
15. Kato, A., Y. Sakai, T. Shioda, T. Kondo, M. Nakanishi, and Y. Nagai. 1996. Initiation of Sendai virus multiplication from transfected cDNA or RNA with negative or positive sense. Genes Cells 1:569-79.
16. Lamb, R. A., and R. M. Krug. 1996. *Orthomyxoviridae*: the viruses and their replication, p. 1353-1395. In B. N. Fields, D. M. Knipe, and P. M. Howley (ed.), Virology, vol. 2. Lippincott-Raven publishers, Philadelphia.
17. Ling, X., and N. Arnheim. 1994. Cloning and identification of the pig ribosomal gene promoter. Gene 150:375-9.
18. Luytjes, W., M. Krystal, M. Enami, J. D. Pavin, and P. Palese. 1989. Amplification, expression, and packaging of foreign gene by influenza virus. Cell 59:1107-13.
19. Neumann, G., and G. Hobom. 1995. Mutational analysis of influenza virus promoter elements in vivo. J Gen Virol 76:1709-17.
20. Neumann, G., T. Watanabe, H. Ito, S. Watanabe, H. Goto, P. Gao, M. Hughes, D. R. Perez, R. Donis, E. Hoffman, G. Hobom, and Y. Kawaoka. 1999. Generation of influenza A viruses entirely from cloned cDNAs. Proc Natl Acad Sci USA 96:9345-9350.
21. Neumann, G., A. Zobel, and G. Hobom. 1994. RNA polymerase I-mediated expression of influenza viral RNA molecules. Virology 202:477-9.
22. Pattnaik, A. K., L. A. Ball, A. W. LeGrone, and G. W. Wertz. 1992. Infectious defective interfering particles of VSV from transcripts of a cDNA clone. Cell 69:1011-20.
23. Paule, M. R., and R. J. White. 2000. Survey and summary: transcription by RNA polymerases I and Ill. Nucleic Acids Res 28:1283-98.
24. Pear, W. S., G. P. Nolan, M. L. Scott, and D. Baltimore. 1993. Production of high-titer helper-free retroviruses by transient transfection. Proc Natl Acad Sci USA 90:8392-6.
25. Pleschka, S., R. Jaskunas, O. G. Engelhardt, T. Zurcher, P. Palese, and A. Garcia-Sastre. 1996. A plasmid-based reverse genetics system for influenza A virus. J Virol 70:4188-92.
26. Rimmelzwaan, G. F., M. Baars, E. C. Claas, and A. D. Osterhaus. 1998. Comparison of RNA hybridization, hemagglutination assay, titration of infectious virus and immunofluorescence as methods for monitoring influenza virus replication in vitro. J Virol Methods 74:57-66.
27. Schnell, M. J., T. Mebatsion, and K. K. Conzelmann. 1994. Infectious rabies viruses from cloned cDNA. Embo J 13:4195-203.
28. Whelan, S. P., L. A. Ball, J. N. Barr, and G. T. Wertz. 1995. Efficient recovery of infectious vesicular stomatitis virus entirely from cDNA clones. Proc Natl Acad Sci USA 92:8388-92.
29. Zobel, A., G. Neumann, and G. Hobom. 1993. RNA polymerase I catalyzed transcription of insert viral cDNA. Nucleic Acids Res 21:3607-14.

Example 2

Recombinant virus is produced as above, based on a high-throughput virus backbone (eg derived from the vaccine strain A/PR/8/34) with the HA and NA genes of a relevant epidemic virus (eg A/Moscow/10/99). After the production of recombinant virus by transfection, the virus is amplified in the appropriate cellular substrate (eg eggs, MDCK cells, Vero cells) to sufficiently high amounts. Upon propagation in embryonated chicken eggs, the allantoic fluid is cleared by centrifugation for 10 min. at 1000× g and filtration through a 0.45 micrometer filter. The virus is now pelleted by centrifugation for 1.5 hours at 150.000× g at 4° C. and resuspended in phosphate-buffered saline (PBS). Virus is subsequently treated with 2% decanoyl-N-methylglucamide (MEGA), loaded on a layer of 25% sucrose in PBS and centrifuged for 1.5 hours at 250.000× g at 4° C.

The top layer containing HA and NA proteins are than dialized against PBS and purity and quantity of the protein preparation are confirmed using 12.5% SDS-polyacrylamide gels stained with coomassie brilliant blue. Ferrets are immunized with ~10 micrograms HA/NA proteins intramuscularly. If desired, vaccinations can be performed using subsequent multiple dosing, or using adjuvants (MF59, ISCOM). Antibody titers against HA and NA in serum samples collected before and after vaccination are determined using hemagglutination inhibition assays, neuraminidase inhibition assays, ELISA, virus neutralization assays, etc. Vaccinated and control animals are challenged 6 weeks after vaccination using 1×10E5 50 percent tissue-culture infectious dosis (TCID-50) of influenza virus A/Moscow/10/99 or a heterologous virus isolate. After challenge, nasal or pharyngeal swab samples are collected from the animals on a daily basis for 10 days, and the amount of virus excreted by the infected animals are determined by quantitative PCR analyses or virus titrations. Thus, the obtained vaccine-induced immunity can be confirmed by quantifying the rise in antibody titers and the level of protection against infection with the challenge virus.

The invention claimed is:
1. A method for producing a replicative influenza virus particle without the use of helper virus, comprising:
    (a) transfecting a cell with at least one nucleic acid, wherein said nucleic acid is chosen from:
    (1) an influenza gene segment and a bacteriophage polymerase promoter; and
    (2) a complement of an influenza gene segment and a bacteriophage polymerase promoter; and
    (b) culturing the transfected cell wherein said cell further comprises a bacteriophage polymerase.
2. The method according to claim 1, wherein said at least one nucleic acid comprises at least one additional guanine residue next to the bacteriophage polymerase promoter.
3. The method according to claim 2, wherein said at least one nucleic acid comprises at least two additional guanine residues next to the bacteriophage polymerase promoter.
4. The method according to claim 1, wherein said at least one nucleic acid lacks a bacteriophage polymerase terminator.
5. The method according to claim 1, wherein said bacteriophage polymerase promoter comprises a T7 polymerase promoter.
6. The method according to claim 1, wherein said cell is transfected with at least seven or eight nucleic acids used in said method.
7. The method according to claim 1, wherein said cell is transfected with a multi-plasmid system.

8. The method according to claim 7, wherein the multiplasmid system comprises twelve unidirectional plasmids expressing eight influenza vRNA nucleic acids, the influenza nucleoprotein, and polymerase proteins PA, PB1, and PB2.

9. The method according to claim 1, wherein at least one said nucleic acid comprises an influenza gene segment that is derived from an influenza virus that is recommended by the World Health Organisation for vaccine purposes.

10. The method according to claim 1, wherein at least one said nucleic acid comprises an influenza A gene segment.

11. The method according to claim 1, wherein said bacteriophage polymerase further comprises a nuclear localization signal.

12. The method according to claim 11, wherein said bacteriophage polymerase is T7 polymerase.

13. The method according to claim 1, wherein said cell comprises a non-primate cell.

14. The method according to claim 13, wherein said cell is chosen from an MDCK cell and a CEF cell.

* * * * *

UNITED STATES PATENT AND TRADEMARK OFFICE
CERTIFICATE OF CORRECTION

| | | |
|---|---|---|
| PATENT NO. | : 7,959,930 B2 | |
| APPLICATION NO. | : 11/722769 | |
| DATED | : June 14, 2011 | |
| INVENTOR(S) | : Emmie De Wit et al. | |

It is certified that error appears in the above-identified patent and that said Letters Patent is hereby corrected as shown below:

In the Title page, item (73), the Assignee's name should read --Abbott Biologicals B.V., Weesp, Netherlands; and Erasmus University Medical Center Rotterdam, Rotterdam, Netherlands-- instead of: "Abbott Biologicals B.V., Weesp, Netherlands".

Signed and Sealed this
Twentieth Day of March, 2012

David J. Kappos
*Director of the United States Patent and Trademark Office*